United States Patent [19]

Takenaka et al.

[11] Patent Number: 5,041,154
[45] Date of Patent: Aug. 20, 1991

[54] BENZOXAZINE COMPOUNDS USEFUL AS HERBICIDES

[75] Inventors: Mitsuaki Takenaka; Seiji Takamura; Masanori Watanabe, all of Ube, Japan

[73] Assignee: Ube Industries, Ltd., Ube, Japan

[21] Appl. No.: 300,742

[22] Filed: Jan. 23, 1989

Related U.S. Application Data

[63] Continuation of Ser. No. 839,324, Mar. 13, 1986, abandoned.

[30] Foreign Application Priority Data

Mar. 22, 1985 [JP] Japan .................. 60-55996

[51] Int. Cl.$^5$ .................. A01N 43/40; C07D 265/36
[52] U.S. Cl. .................. 71/88; 544/105
[58] Field of Search .................. 544/105; 71/88

[56] References Cited

U.S. PATENT DOCUMENTS

| | | | |
|---|---|---|---|
| 4,164,576 | 8/1979 | Carr | 544/105 |
| 4,252,804 | 2/1981 | Joullié et al. | 514/237.5 |
| 4,574,124 | 3/1986 | Kabbe et al. | 544/105 |
| 4,618,561 | 10/1986 | Moser | 71/88 |

Primary Examiner—Mukund J. Shah
Assistant Examiner—Jyothsna Venkat
Attorney, Agent, or Firm—Frishauf, Holtz, Goodman & Woodward

[57] ABSTRACT

There are disclosed a 3,4-dihydro-2H-1,4-benzoxazine derivatives represented by the formula:

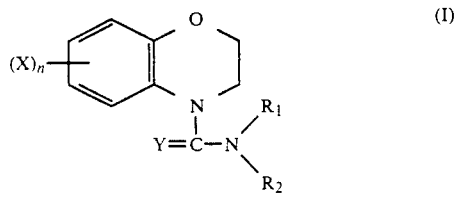

wherein X represents a hydrogen atom, an alkyl group having 1 to 5 carbon atoms, a halogen atom, a trifluoromethyl group, a phenoxy group, or a halogen-substituted phenoxy group; n is 0, 1, 2 or 3; Y represents an oxygen atom or a sulfur atom; and $R_1$ and $R_2$ each represent a hydrogen atom or an alkyl group having 1 to 5 carbon atom, provided that the case where both of $R_1$ and $R_2$ are hydrogen atoms is excluded, and a herbicidal composition containing the same as an active ingredient, useful for combatting weeds.

19 Claims, No Drawings

BENZOXAZINE COMPOUNDS USEFUL AS HERBICIDES

This application is a continuation of application Ser. No. 06/839,324, filed Mar. 13, 1986, now abandoned.

BACKGROUND OF THE INVENTION

This invention relates to a benzoxazine derivative and a herbicidal composition containing the same as an active ingredient.

More specifically, this invention relates to a 3,4-dihydro-2H-1,4-benzoxazine derivative represented by the following formula:

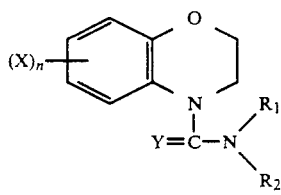

wherein X represents a hydrogen atom, an alkyl group having 1 to 5 carbon atoms, a halogen atom, a trifluoromethyl group, a phenoxy group or a halogen-substituted phenoxy group; n is 0, 1, 2 or 3; Y represents an oxygen atom or a sulfur atom; and $R_1$ and $R_2$ each represent a hydrogen atom or an alkyl group having 1 to 5 carbon atom, provided that the case where both of $R_1$ and $R_2$ are hydrogen atoms is excluded, and a herbicidal composition containing the above as active ingredients.

In recent years, a role of a herbicidal composition in cultivation of crops has remarkably been enhanced and the herbicidal composition has contributed to an increment of yield, improvement of quality and improvement of productivity. On the other hand, problems has been revealed that weeds which are not damaged by conventional herbicidal composition will tend to increase and a damage from agricultural chemicals will happen, and thus it has been desired to improve the characteristics of a herbicidal composition.

SUMMARY OF THE INVENTION

The present inventors have intensively researched to solve the above problems and as a result, have found that 3,4-dihydro-2H-1,4-benzoxazine derivatives have excellent herbicidal effect against various kinds of cultivated land's weeds without causing damage from agricultural chemicals to many available crops, and have accomplished the present invention.

That is, the present invention is to provide 3,4-dihydro-2H-1,4-benzoxazine derivatives represented by the formula:

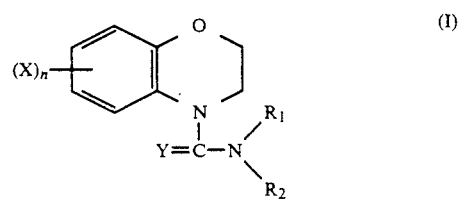

wherein X represents a hydrogen atom, an alkyl group having 1 to 5 carbon atoms, a halogen atom, a trifluoromethyl group, a phenoxy group, or a halogen-substituted phenoxy group; n is 0, 1, 2 or 3; Y represents an oxygen atom or a sulfur atom; and $R_1$ and $R_2$ each represent a hydrogen atom or an alkyl group having 1 to 5 carbon atom, provided that the case where both of $R_1$ and $R_2$ are hydrogen atoms is excluded, and a herbicidal composition containing the same as active ingredients.

PREFERRED EMBODIMENTS OF THE INVENTION

In the 3,4-dihydro-2H-1,4-benzoxazine derivatives having the above formula (I), preferred compound is represented by the formula shown below:

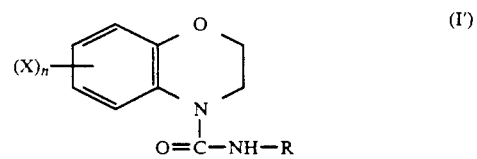

wherein X represents an alkyl group having 1 to 5 carbon atoms, a halogen atom or a trifluoromethyl group; n is 1 or 2; and R represents an alkyl group having 1 to 5 carbon atom.

Specific examples of 3,4-dihydro-2H-1,4-benzoxazine derivatives having the above formula of the present invention are shown in Table 1.

TABLE 1

| Compound No. | Chemical structure | Physical property |
|---|---|---|
| 1 | ![structure] | m.p. 103–104° C. |
| 2 | ![structure] | m.p. 95.3° C. |

TABLE 1-continued

| Compound No. | Chemical structure | Physical property |
|---|---|---|
| 3 | 4-CH₃, benzoxazine, N-C(=O)-NHCH₃ | m.p. 124-126° C. |
| 4 | 5-CH₃, benzoxazine, N-C(=O)-NHCH₃ | m.p. 85-86° C. |
| 5 | n-C₄H₉ substituted benzoxazine, N-C(=O)-NHCH₃ | m.p. 71.9° C. |
| 6 | n-C₄H₉ substituted benzoxazine, N-C(=O)-N(CH₃)₂ | $n_D^{24}$ 1.5488 |
| 7 | (CH₃)₂CH- substituted benzoxazine, N-C(=O)-NHCH₃ | m.p. 85.0° C. |
| 8 | (CH₃)₂CH- substituted benzoxazine, N-C(=O)-NHCH₃ | m.p. 130~133° C. |
| 9 | (CH₃)₃C- substituted benzoxazine, N-C(=O)-NHCH₃ | m.p. 151~153° C. |
| 10 | (CH₃)₃C- substituted benzoxazine, N-C(=O)-NHCH(CH₃)₂ | m.p. 123.6° C. |
| 11 | CF₃ substituted benzoxazine, N-C(=O)-NHCH₃ | m.p. 94~96° C. |

TABLE 1-continued

| Compound No. | Chemical structure | Physical property |
| --- | --- | --- |
| 12 | 6-fluoro-3,4-dihydro-2H-1,4-benzoxazine-4-carboxylic acid methylamide | m.p. 107~108° C. |
| 13 | 6-chloro-3,4-dihydro-2H-1,4-benzoxazine-4-carboxylic acid methylamide | m.p. 123~124° C. |
| 14 | 6-chloro-3,4-dihydro-2H-1,4-benzoxazine-4-carboxylic acid dimethylamide | m.p. 99.1° C. |
| 15 | 6-bromo-3,4-dihydro-2H-1,4-benzoxazine-4-carbonyl ethyl | m.p. 130~131° C. |
| 16 | 7-bromo-3,4-dihydro-2H-1,4-benzoxazine-4-carboxylic acid methylamide | m.p. 102~104° C. |
| 17 | 6-phenoxy-3,4-dihydro-2H-1,4-benzoxazine-4-carboxylic acid methylamide | m.p. 128~129° C. |
| 18 | 6-chloro-7-methyl-3,4-dihydro-2H-1,4-benzoxazine-4-carboxylic acid methylamide | m.p. 142~143.5° C. |
| 19 | 6-chloro-7-methyl-3,4-dihydro-2H-1,4-benzoxazine-4-carboxylic acid ethylamide | m.p. 117~118° C. |
| 20 | 6-chloro-7-methyl-3,4-dihydro-2H-1,4-benzoxazine-4-carboxylic acid dimethylamide | m.p. 78~81° C. |

TABLE 1-continued
| Compound No. | Chemical structure | Physical property |
|---|---|---|
| 21 | 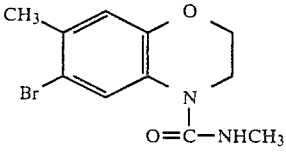 | m.p. 155.3° C. |
| 22 | 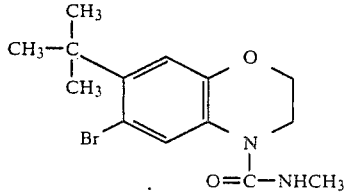 | m.p. 163~166° C. |
| 23 | 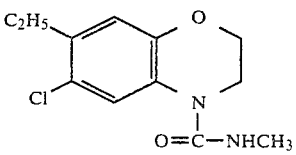 | m.p. 147.6° C. |
| 24 | 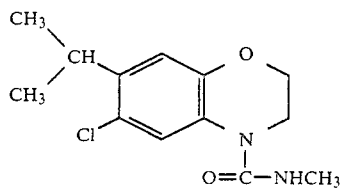 | m.p. 144~146° C. |
| 25 | 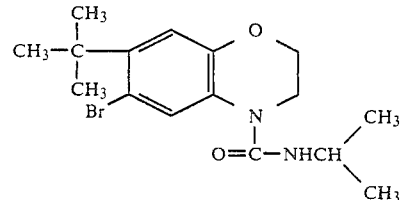 | m.p. 203.1° C. |
| 26 | 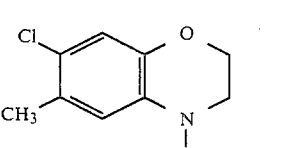 | m.p. 119~120° C. |
| 27 | 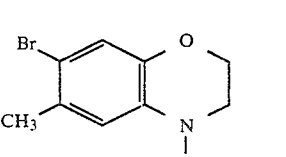 | m.p. 127.8° C. |
| 28 | 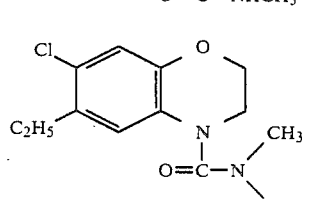 | $n_D^{24}$ 1.5713 |
| 29 | 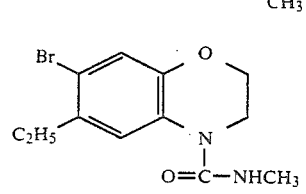 | m.p. 116~117° C. |

TABLE 1-continued
| Compound No. | Chemical structure | Physical property |
|---|---|---|
| 30 | 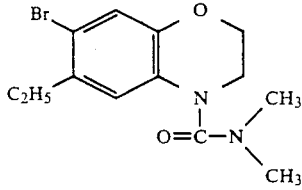 | $n_D^{24}$ 1.5868 |
| 31 | 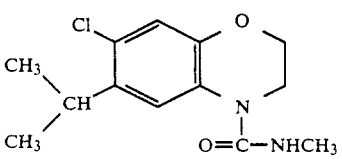 | m.p. 120.2° C. |
| 32 | 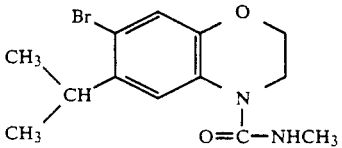 | m.p. 139.1° C. |
| 33 | 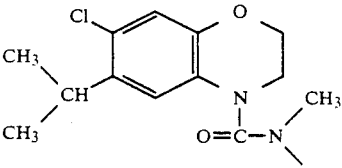 | m.p. 110.1° C. |
| 34 | 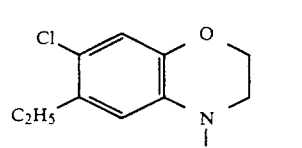 | m.p. 88.3° C. |
| 35 | 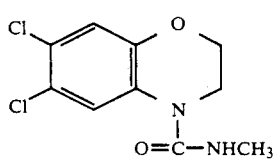 | m.p. 142~143° C. |
| 36 | 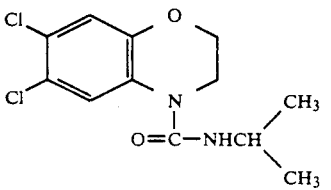 | m.p. 108~109° C. |
| 37 | 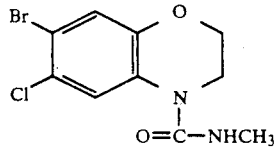 | m.p. 128~129° C. |
| 38 | 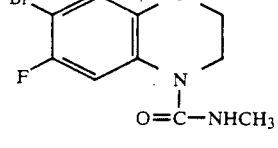 | m.p. 148~149° C. |

TABLE 1-continued

| Compound No. | Chemical structure | Physical property |
|---|---|---|
| 39 | 4-bromophenoxy, Br-substituted benzoxazine with N-C(=O)-NHCH₃ | m.p. 137~140° C. |
| 40 | CH₃, Cl-substituted benzoxazine with N-C(=O)-NHCH₃ | m.p. 104~105° C. |
| 41 | Cl, Cl-substituted benzoxazine with N-C(=O)-N(CH₃)₂ | m.p. 113.1° C. |
| 42 | Cl, Cl-substituted benzoxazine with N-C(=O)-NHCH₃ | m.p. 150.5° C. |
| 43 | CH₃, Br, Cl-substituted benzoxazine with N-C(=O)-NHCH₃ | m.p. 172.1° C. |
| 44 | CH₃, Cl, Cl-substituted benzoxazine with N-C(=O)-NHCH₃ | m.p. 164.9° C. |
| 45 | Cl, Br, Cl-substituted benzoxazine with N-C(=O)-NHCH₃ | m.p. 186-189° C. |
| 46 | CH₃, Cl-substituted benzoxazine with N-C(=S)-NHCH₃ | m.p. 171.3° C. |

Among the above compounds, particularly preferred are those shown below:

7-isopropyl-4-(N-methylcarbamoyl)-3,4-dihydro-2H-1,4-benzoxazine (compound of Compound No. 8);

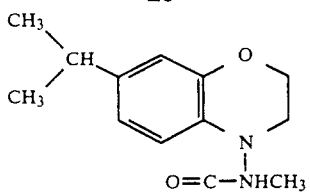

6-trifluoromethyl-4-(N-methylcarbamoyl)-3,4-dihydro-2H-1,4-benzoxazine (compound of Compound No. 11);

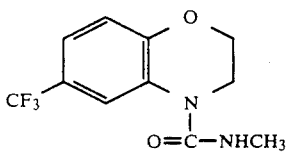

6-chloro-7-methyl-4-(N-methylcarbamoyl)-3,4-dihydro-2H-1,4-benzoxazine (compound of Compound No. 18);

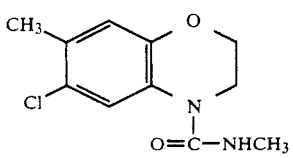

6,7-dichloro-4-(N-methylcarbamoyl)-3,4-dihydro-2H-1,4-benzoxazine (compound of Compound No. 35);

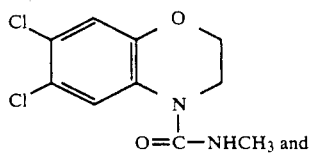

7-bromo-6-chloro-4-(N-methylcarbamoyl)-3,4-dihydro-2H-1,4-benzoxazine (compound of Compound No. 37);

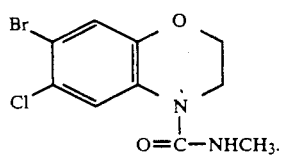

As examples of the method for preparing these 3,4-dihydro-2H-1,4-benzoxazine derivatives of the present invention, there may be mentioned the following reaction (1) or (2):

Reaction (1):

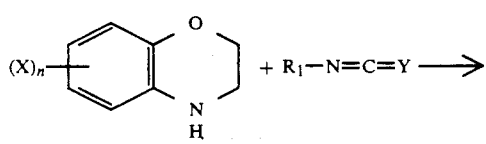

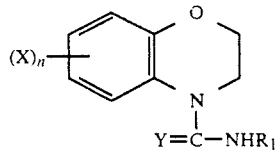

Reaction (2):

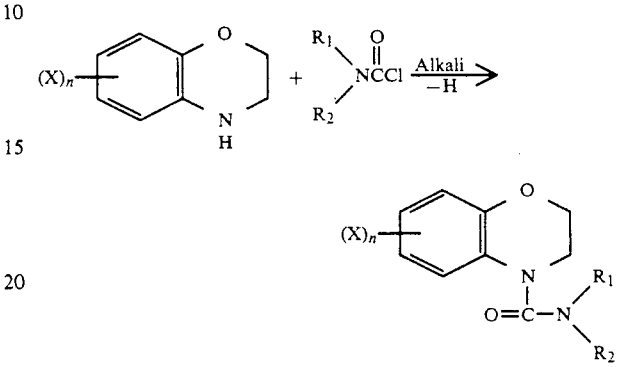

wherein X, n, Y, $R_1$ and $R_2$ have the same meanings as defined in the formula (I).

The above reaction (1) can be carried out in an aromatic hydrocarbon such as benzene, toluene, xylene, etc.; an ether such as diethylether, tetrahydrofuran, dioxane, etc.; and a ketone such as methyl ethyl ketone, dimethyl ketone, etc., at a reaction temperature of 0° to 110° C. and a reaction time of 1 to 10 hours.

On the other hand, the above reaction (2) can be carried out in an aromatic hydrocarbon such as benzene, toluene, xylene, etc.; and a ketone such as methyl ethyl ketone, dimethyl ketone, etc., with the addition of a weak alkali such as pyridine, triethyl amine, sodium carbonate, potassium carbonate, etc. at a reaction temperature of 50° to 130° C. and a reaction time of 1 to 10 hours.

Next, exemplary synthesis examples of the present invention are mentioned.

Synthesis example 1

Synthesis of 6-chloro-7-methyl-4-(N-methylcarbamoyl)-3,4-dihydro-2H-1,4-benzoxazine (compound of Compound No. 18)

In 20 ml of toluene was dissolved 1.7 g (0.01 mole) of 6-chloro-7-methyl-3,4-dihydro-2H-1,4-benzoxazine, and 0.5 g (0.14 mole) of methyl isocyanate was added thereto. After the reaction at 50° C. for 3 hours, toluene and excessive methyl isocyanate were distilled out. Resulting crude crystal was recrystallized from toluene to obtain 1.3 g of colorless needle-like crystal having a melting point of 142° to 143° C. It was confirmed that the resulting crystal was the title compound by using NMR, IR and elemental analysis. A yield based on 6-chloro-7-methyl-3,4-dihydro-2H-1,4-benzoxazine was 54 %.

Synthesis example 2

Synthesis of 6-chloro-4-(N,N-dimethylcarbamoyl)-3,4-dihydro-2H-1,4-benzoxazine (compound of Compound No. 14)

In 50 ml of acetone were dissolved 3.1 g (0.02 mole) of 6-chloro-3,4-dihydro-2H-1,4-benzoxazine and 2.6 g (0.024 mole) of N,N-dimethylcarbamoyl chloride, and then 2.8 g (0.026 mole) of anhydrous potassium carbonate was added thereto and the mixture was boiled and refluxed for 10 hours under stirring. After cooling, acetone was distilled out and 150 ml of water was added to the residue and precipitated oily product was extracted with toluene. The extracted toluene layer was successively washed with diluted hydrochloric acid, diluted sodium hydroxide and water and dehydrated, and then toluene was distilled out. Resulting crude crystal was recrystallized from a mixed solution of toluene and hexane to obtain 1.5 g of colorless powdery crystal having a melting point of 99.1° C. It was confirmed that the resulting crystal was the title compound by using NMR, IR and elemental analysis. A yield based on 6-chloro-3,4- dihydro-2H-1,4-benzoxazine was 31%.

Synthesis example 3

Synthesis of 6-chloro-7-methyl-4-(N-methylthiocarbamoyl)-3,4-dihydro-2H-1,4-benzoxazine (compound of Compound No. 46)

In 20 ml of toluene was dissolved 1.7 g (0.01 mole) of 6-chloro-7-methyl-3,4-dihydro-2H-1,4-benzoxazine, and 0.9 g (0.123 mole) of methyl isothiocyanate was added thereto. After the reaction at 50° C. for 3 hours, toluene and excessive methyl isothiocyanate were distilled out. Resulting crude crystal was recrystallized from toluene to obtain 1.3 g of colorless powdery crystal having a melting point of 171.3° C. It was confirmed that the resulting crystal was the title compound by using NMR, IR and elemental analysis. A yield based on 6-chloro-7-methyl-3,4-dihydro-2H-1,4-benzoxazine was 51 %.

When the 3,4-dihydro-2H-1,4-benzoxazine derivative of the present invention is to be applied as a herbicidal composition, the derivative may be formulated for use to the preparations of any form commonly employed as the agricultural formulation, by using an inert solid carrier, liquid carrier, emulsifying dispersant and the like, for example, granules, dusts, emulsions, wettable powders, tablets, lubricants, aerosols, fumigants and so on. As the inert carrier, there may be mentioned, for example, talc, clay, kaoline, diatomaceous earth, calcium carbonate, potassium chlorate, saltpeter, wood powder, nitrocellulose, starch, benzene, xylene, n-hexane, gum arabic, vinyl chloride, carbon dioxide, fleon, propane, butane and the like. Further, it may also optionally be blended with any auxiliary agents for preparation, for example, spreaders, diluents, surface active agents, solvents and the like. Moreover, it may also be optionally admixed with fungicides, insecticides and other herbicides; urea, ammonium sulfate, ammonium phosphate, potassium salts and other fertilizers; soil conditioners and the like.

Next, Examples of the herbicidal composition of the present invention are given below. All parts in each examples are given by parts by weight hereinafter unless otherwise stated.

EXAMPLE 1

8 parts of 6-chloro-7-methyl-4-(N-methylcarbamoyl)-3,4-dihydro-2H-1,4-benzoxazine (compound of Compound No. 18), 30 parts of bentonite, 59 parts of talc, 1 part of Neopelex powder (trade name, produced by Kao Atlas Co., Ltd.) and 2 parts of sodium lignosulfonate were homogeneously blended and, after addition of a small amount of water, kneaded and then granulated and dried to give granules.

EXAMPLE 2

50 parts of 6-bromo-7-methyl-4-(N-methylcarbamoyl)-3,4-dihydro-2H-1,4-benzoxazine (compound of Compound No. 21), 48 parts of kaolin and 2 parts of Neopelex powder were homogeneously blended and pulverized to obtain a wettable powder.

EXAMPLE 3

50 parts of 6-bromo-7-t-butyl-4-(N-methylcarbamoyl)-3,4-dihydro-2H-1,4-benzoxazine (compound of Compound No. 22), 40 parts of xylene, 5 parts of dimethylformamide and 5 parts of Toxanone (trade name, produced by Sanyo Kasei Kogyo Co., Ltd.) were homogeneously mixed and dissolved to obtain an emulsion.

EXAMPLE 4

5 parts of 6,7-dichloro-4-(N-methylcarbamoyl)-3,4-dihydro-2H-1,4-benzoxazine (compound of Compound No. 35), 50 parts of talc and 45 parts of kaolin were homogeneously mixed to obtain a dust.

Next, the effects of the herbicidal composition according to the present invention will be explained concretely by way of Experiments shown below. The number of each test compound in each Experiment is the same as that in Table 1 shown above.

Experiment 1

Soil treatment tests for paddy field weed

Wagner pots, each having an area of 1/5000 are, were packed with Ube soil (diluvial soil) and planted with dormant awakening seeds of barnyard grass (*Echinochloa crusgalli*), roots of flatstage (*Cyperus serotinus*), arrowhead (*Sagittaria pygmaea*) and slender spikerush (*Eleocharis acicularis*) and, after covering up seeds with soil, seeds of monochoria (*Monochoria vaginalis*) and hotarui (*Scripus juncoides*) were sowed on the upper layer thereof. Afterward, the pots were filled with water to a depth of 3 cm. Then, each test compound (a wettable powder prepared according to Example 2 was diluted with water so as to become the concentration of the active ingredient being 1000 ppm) was spread to the surface of filled water by dropwise addition treatment by using pipet so as to have an amount of the active ingredient being 50 g/a and they were controlled in a glass house having an average temperature of 25° C. Three weeks after the treatment, the herbicidal effects of each test compound were assessed. The results are shown in Table 2.

In Table 2, the herbicidal effects are evaluated according to the following standards:
5 : All killed, 4 : Severely damaged,
3 : Moderately damaged, 2 : Slightly damaged,
1 : Minor damaged, and 0 : None (normal development).

TABLE 2

| Compound No. | Echinochloa crusgalli | Monochoria vaginalis | Eleocharis acicularis | Cyperus serotinus | Scripus juncoides | Sagittaria pygmaea |
|---|---|---|---|---|---|---|
| 6 | 4 | 5 | 0 | 0 | 3 | 0 |
| 8 | 5 | 5 | 5 | 5 | 5 | 2 |
| 9 | 5 | 5 | 5 | 3 | 4 | 3 |
| 11 | 5 | 5 | 5 | 5 | 5 | 5 |
| 12 | 5 | 5 | 5 | 3 | 5 | 5 |
| 13 | 5 | 5 | 5 | 4 | 5 | 5 |
| 15 | 5 | 5 | 5 | 2 | 5 | 4 |

TABLE 2-continued

| Compound No. | Echino- chloa crus- galli | Mono- choria vagina- lis | Eleo- charis acicu- laris | Cype- rus sero- tinus | Scri- pus jun- coides | Sagitta- ria pygmaea |
|---|---|---|---|---|---|---|
| 16 | 5 | 5 | 5 | 2 | 5 | 5 |
| 17 | 2 | 5 | 2 | 1 | 0 | 1 |
| 18 | 5 | 5 | 5 | — | 4 | 2 |
| 19 | 5 | 5 | 5 | 0 | 5 | 2 |
| 20 | 5 | 5 | 2 | — | 5 | — |
| 21 | 5 | 5 | 5 | 5 | 5 | 4 |
| 22 | 5 | 5 | 5 | 3 | 4 | 3 |
| 23* | 5 | — | — | 2 | 5 | 5 |
| 24* | 5 | — | — | 5 | 5 | 5 |
| 26 | 5 | 5 | 5 | 3 | 5 | 1 |
| 27 | 5 | 5 | 5 | 0 | 5 | 5 |
| 35 | 5 | 5 | 5 | 4 | 5 | 4 |
| 36 | 2 | 5 | 0 | 0 | 5 | 2 |
| 37 | 5 | 5 | 5 | 5 | 5 | 5 |
| 38 | 5 | 5 | 5 | 3 | 5 | 2 |
| 39 | 4 | 5 | 3 | 5 | 4 | 3 |
| 40 | 5 | 5 | 5 | 0 | 4 | 2 |
| 41 | 4 | 5 | 0 | 0 | 0 | 0 |
| 42 | 5 | 5 | 5 | 5 | 5 | 2 |
| 43* | 5 | — | — | 1 | 5 | 5 |
| 44* | 5 | — | — | 5 | 5 | 5 |
| 46 | 3 | 5 | 0 | 0 | 3 | 0 |
| Reference compd. 1 | 1 | 0 | 0 | 0 | 0 | 0 |
| Reference compd. 2 | 0 | 0 | 0 | 0 | 0 | 0 |

*Amount of effective ingredient is 20 g/a.
Reference compound 1: 1-(N-methylcarbamoyl-2,3-dihydroindole
Reference compound 2: 1-(N-methylcarbamoyl)-1,2,3,4-tetrahydroquinoline Experiment 2

Soil treatment tests for upland weed

Wagner pots, each having an area of 1/3000 are, were packed with Ube soil and then seeds of Manna-grass (*Digitaria sanguinalis*),
Barnyard grass (*Echinochloa crusgalli*),
Redroot pigweed (*Amaranthus retroflexus*),
White goose-foot (*Chenopodium album*),
Tall morningglory (*Ipomoea purpurea*), and
Sickle pod (*Cassia tora*)

were sowed therein. After covering seeds with soil, each herbicidal compound (a wettable powder prepared according to Example 2 was diluted with water so as to become the concentration of the active ingredient being 1000 ppm) was uniformly spread on the surface layer thereof so as to have an amount of the active ingredient being 50 g/a by using a pressure sprayer and they were controlled in a glass house having an average temperature of 25° C. Three weeks after the treatment, the herbicidal effects of each test compound were assessed. The results are shown in Table 3.

In Table 3, the same rating system as defined in Experiment 1 is applied.

TABLE 3

| Compound No. | Digi- taria sangui- nalis | Echino- chloa crus- galli | Amaran- thus retro- flexus | Cheno- podium album | Ipo- moea pur- purea | Cas- sia tora |
|---|---|---|---|---|---|---|
| 1 | 3 | 3 | 5 | 5 | 3 | 1 |
| 2 | 4 | 3 | 5 | 5 | 2 | — |
| 3 | 5 | 3 | 5 | 5 | 3 | 1 |
| 4 | 0 | 0 | 4 | 4 | 0 | 0 |
| 8 | 5 | 4 | 5 | 5 | 2 | — |
| 9 | 5 | 4 | 4 | 5 | 3 | 5 |
| 11 | 5 | 5 | 5 | 5 | 5 | 4 |
| 12 | 5 | 5 | 5 | 4 | 4 | 3 |
| 13 | 5 | 3 | 5 | 4 | 3 | 2 |
| 14 | 4 | 2 | 3 | 4 | 4 | 1 |

TABLE 3-continued

| Compound No. | Digi- taria sangui- nalis | Echino- chloa crus- galli | Amaran- thus retro- flexus | Cheno- podium album | Ipo- moea pur- purea | Cas- sia tora |
|---|---|---|---|---|---|---|
| 15 | 5 | 2 | 5 | 5 | 1 | 0 |
| 18 | 5 | 5 | 5 | 5 | 5 | 5 |
| 20 | 5 | 4 | 5 | 5 | — | — |
| 21 | 5 | 3 | 5 | 4 | 0 | 0 |
| 22 | 4 | 0 | 5 | 5 | 1 | 1 |
| 23* | 5 | 5 | 5 | 5 | 0 | 2 |
| 24* | 5 | 5 | 5 | 5 | 5 | 0 |
| 26 | 4 | 2 | 5 | 5 | 0 | 0 |
| 35 | 5 | 3 | 5 | 5 | 3 | 1 |
| 37 | 5 | 1 | 5 | 5 | 0 | 1 |
| 38 | 4 | 2 | 5 | 4 | 1 | 2 |
| 40 | 5 | 3 | 5 | 5 | 1 | 0 |
| 42 | 5 | 4 | 5 | 4 | 0 | 0 |
| 44* | 5 | 2 | 5 | 5 | 0 | 0 |
| 45* | 5 | 3 | 1 | 5 | 1 | 1 |
| 46 | 5 | 1 | 5 | 5 | 0 | 0 |
| Reference compd. 1 | 3 | 0 | 3 | 4 | 0 | 0 |
| Reference compd. 2 | 0 | 0 | 1 | 4 | 0 | 0 |

*Amount of effective ingredient is 20 g/a.
Reference compounds 1 and 2 are the same as in Table 2.

Experiment 3

Foliar treatment tests for upland weed

Wagner pots, each having an area of 1/5000 are, were packed with Ube soil and then the following plants were reared:

Manna-grass (*Digitaria sanguinalis*) 2 leaf stage,
Barnyard grass (*Echinochloa crusgalli*) 2 leaf stage,
Cocklebur (*Xanthium strumarium*) 1 leaf stage,
Wild mustard (*Brassica kaber*) 2 leaf stage,
Tall morningglory (*Ipomoea purpurea*) 1 leaf stage, and
Sickle pod (*Cassia tora*) 1 leaf stage.

A wettable powder of each herbicidal compound was diluted to 0.5% by weight with water containing 100 ppm of Neoesterin (trade name, produced by Kumiai Kagaku Co., Ltd.) as a wetting agent and was uniformly sprayed on the foliage of the weeds with 5 ml per one pot by using a pressure sprayer and they were controlled in a glass house having an average temperature of 25° C. Three weeks after the treatment, the herbicidal effects of each test compound were assessed. The results are shown in Table 4.

In Table 4, the same rating system as defined in Experiment 1 is applied.

TABLE 4

| Compound No. | Digi- taria sangui- nalis | Echino- chloa crus- galli | Xan- thium struma- rium | Bras- sica kaber | Ipo- moea pur- purea | Cas- sia tora |
|---|---|---|---|---|---|---|
| 1 | 1 | 2 | 5 | 3 | 5 | 4 |
| 2 | 3 | 2 | 5 | 5 | 5 | 4 |
| 3 | 5 | 3 | 5 | 5 | 5 | 5 |
| 4 | 1 | 1 | 5 | 2 | 2 | 2 |
| 8 | 5 | 5 | 5 | 5 | 5 | 5 |
| 9 | 5 | 5 | 5 | 5 | 5 | 5 |
| 11 | 5 | 5 | 5 | 5 | 5 | 5 |
| 12 | 5 | 2 | 5 | 5 | 5 | 5 |
| 13 | 5 | 5 | 5 | 5 | 5 | 5 |
| 14 | 3 | 1 | 5 | 3 | 5 | 4 |
| 15 | 5 | 5 | 5 | 5 | 5 | 5 |
| 16 | 5 | 5 | 5 | 5 | 5 | 5 |
| 17 | 1 | 0 | 5 | 5 | 4 | 1 |
| 18 | 5 | 5 | 5 | 5 | 5 | 5 |
| 19 | 5 | 5 | 5 | 5 | 5 | 5 |
| 20 | 5 | 5 | — | 5 | 5 | — |

TABLE 4-continued

| Compound No. | Digitaria sanguinalis | Echinochloa crusgalli | Xanthium strumarium | Brassica kaber | Ipomoea purpurea | Cassia tora |
|---|---|---|---|---|---|---|
| 21 | 5 | 3 | 5 | 5 | 5 | 5 |
| 22 | 5 | 5 | 5 | 5 | 5 | 5 |
| 23* | 5 | 4 | — | — | 5 | 5 |
| 24* | 5 | 5 | — | — | 5 | 5 |
| 26 | 5 | 5 | 5 | 5 | 5 | 5 |
| 27 | 5 | 4 | 5 | 5 | 5 | 5 |
| 35 | 5 | 5 | 5 | 5 | 5 | 5 |
| 37 | 5 | 5 | 5 | 5 | 5 | 5 |
| 38 | 5 | 5 | 5 | 5 | 5 | 5 |
| 39 | 2 | 1 | 5 | 5 | 5 | 5 |
| 40 | 5 | 5 | 5 | 5 | 5 | 5 |
| 41 | 1 | 0 | 5 | 5 | 5 | 5 |
| 42 | 3 | 3 | 5 | 5 | 5 | 5 |
| 43 | 4 | 4 | 5 | 5 | 5 | 5 |
| 44 | 5 | 5 | 5 | 5 | 5 | 5 |
| 45* | 1 | 3 | — | — | 5 | 5 |
| 46 | 5 | 3 | 5 | 5 | 5 | 5 |
| Reference compd. 1 | 1 | 0 | 4 | 4 | 4 | 3 |
| Reference compd. 2 | 0 | 0 | 0 | 0 | 2 | 0 |

*Concentration of effective ingredient is 0.2%.
Reference compounds 1 and 2 are the same as in Table 2.

Experiment 4

Soil treatment low active ingredient tests for upland weed

Wagner pots, each having an area of 1/5000 are, were packed with Ube soil and then seeds of:
Corn (*Zea mays*),
Sorghum (*Sorghum bicolor*),
Barley (*Hordeum vulgare*),
Wheat (*Triticum aestivum*),
Soybean (*Glycine max*),
Cotton (*Gossypium hirusutum*),
Manna-grass (*Digitaria sanguinalis*),
Foxtail (*Alopecurus aequalis*),
White goose-foot (*Chenopodium album*),
Redroot pigweed (*Amaranthus retroflexus*),
Indian mallow (*Abutilon theophrasti*),
Prickly sida (*Sida spinosa*),
Henbit (*Lamium amplexicaule*),
White-bird's-eye (*Stellaria media*) and
Wild mustard (*Brassica kaber*)
were sowed therein by dividing into two pots and, after covering seeds with soil, each herbicidal compound (a wettable powder prepared according to Example 2 was diluted with water so as to become the concentration of the active ingredient being 1000 ppm) was uniformly spread on the surface layer thereof so as to have an amount of the active ingredient being 10 and 5 g/a by using a pressure sprayer and they were controlled in a glass house having an average temperature of 25° C. Three weeks after the herbicidal compound treatment, the herbicidal effects of each test compound were assessed. The results are shown in Table 5.

In Table 5, the same rating system as defined in Experiment 1 is applied.

TABLE 5

| Compound | 18 | | 35 | | 37 | |
|---|---|---|---|---|---|---|
| Amount (g/a) | 10 | 5 | 10 | 5 | 10 | 5 |
| Zea mays | 0 | 0 | 0 | 0 | 0 | 0 |
| Sorghum bicolor | 0 | 0 | 0 | 0 | 0 | 0 |
| Hordeum vulgare | 0 | 0 | 0 | 0 | 0 | 0 |
| Triticum aestivum | 2 | 0 | 0 | 0 | 0 | 0 |
| Glycine max | 5 | 1 | 0 | 0 | 0 | 0 |
| Gossypium herusutum | 0 | 0 | 0 | 0 | 0 | 0 |
| Digitaria sanguinalis | 5 | 5 | 5 | 5 | 5 | 5 |
| Alopecurus aequalis | 5 | 2 | 5 | 3 | 5 | 3 |
| Chenopodium album | 5 | 5 | 5 | 5 | 5 | 5 |
| Amaranthus retroflexus | 5 | 5 | 5 | 5 | 5 | 5 |
| Abutilon theophrasti | 5 | 5 | 5 | 4 | 5 | 5 |
| Sida spinosa | 5 | 5 | 5 | 5 | 5 | 5 |
| Lamium amplexicaule | 5 | 5 | 5 | 4 | 5 | 5 |
| Stellaria media | 5 | 5 | 5 | 5 | 5 | 5 |
| Brassica kaber | 5 | 5 | 5 | 5 | 5 | 5 |

Experiment 5

Foliar treatment low active ingredient tests for upland weed

Wagner pots, each having an area of 1/5000 are, were packed with Ube soil and then the following plants were sowed therein and reared by dividing into two pots:
Corn (*Zea mays*),
Wheat (*Triticum aestivum*),
Manna-grass (*Digitaria sanguinalis*),
Foxtail (*Alopecurus aequalis*),
White goose-foot (*Chenopodium album*),
Redroot pigweed (*Amaranthus retroflexus*),
Indian mallow (*Abutilon theophrasti*),
Prickly sida (*Sida spinosa*),
Henbit (*Lamium amplexicaule*),
White-bird's-eye (*Stellaria media*) and
Wild mustard (*Brassica kaber*)

At the time when each of plants were reached to the leaf stage as shown in Table 6, a wettable powder of each herbicidal compound was diluted to 0.05 and 0.025% by weight with water containing 100 ppm of Neoesterin (trade name, produced by Kumiai Kagaku Co., Ltd.) as a wetting agent and was uniformly sprayed on the foliage with each 5 ml per one pot by using a pressure sprayer and they were controlled in a glass house having an average temperature of 25° C. Three weeks after the treatment, the herbicidal effects of each test compound were assessed. The results are shown in Table 6.

In Table 6, the same rating system as defined in Experiment 1 is applied.

TABLE 6

| Compound No. | 18 | | 37 | | Leaf stage at treatment |
|---|---|---|---|---|---|
| Concentration (%) | 0.05 | 0.025 | 0.05 | 0.025 | |
| Zea mays | 1 | 0 | — | 2 | 2 to 3 leaf |
| Triticum aestivum | 1 | 1 | 1 | 1 | 2 to 3 leaf |
| Digitaria sanguinalis | 5 | 5 | 5 | 3 | 3 to 4 leaf |
| Alopecurus aequalis | 5 | 5 | 4 | 4 | 3 leaf |
| Chenopodium album | 5 | 5 | 5 | 5 | 4 to 6 leaf |
| Amaranthus retroflexus | 5 | 5 | 5 | 5 | 2 to 3 leaf |
| Abutilon theophrasti | 5 | 5 | 5 | 5 | 2 to 3 leaf |
| Sida spinosa | 5 | 5 | 5 | 5 | 2 to 3 leaf |
| Lamium amplexicaule | 5 | 5 | 5 | 5 | 2 leaf |

TABLE 6-continued

| Compound No. | 18 | | 37 | | Leaf stage at |
|---|---|---|---|---|---|
| Concentration (%) | 0.05 | 0.025 | 0.05 | 0.025 | treatment |
| Stellaria media | 5 | 5 | 5 | 5 | 2 to 4 leaf |
| Brassica kaber | 5 | 5 | 5 | 5 | 4 leaf |

As described above, 3,4-dihydro-2H-1,4-benzoxazine derivatives of the present invention has, in rising various crops such as corn, sorghum, barley, wheat, soybean, cotton, etc., excellent herbicidal effect in both treatments of the soil treatment before germination and the cormophyte treatment against the weeds of grasses such as foxtail, barnyard grass, etc.; and the various broadleaf weeds such as wild mustard, cocklebur, sickle pod, tall morningglory, white goose-foot, redroot pigweed, etc., and has less damage from agricultural chemicals (see Tables 3, 4, 5 and 6). Further, it has also an excellent herbicidal effect against the paddy field weeds (see Table 2).

As a urea series herbicidal composition which is formed a ring between an ortho-position of a benzene ring and a nitrogen atom of a ureido group according to the compound of the present invention, a herbicidal activity of a N-carbamoyl-2,3-dihydroindole derivative has been reported (Far maco, Ed Sci. Vol. 31, pp. 746-757, 1976 CA 86, 55235m; and ibid. Vol. 32, pp. 54-66, 1977 CA 86, 139742n), but the compounds are remarkably inferior in activity to the benzoxazine derivative of the present invention (see Tables 2, 3 and 4).

The compound of the present invention is a typical photosynthesis inhibitor which inhibits Hill reaction which is the light reaction of photosynthesis in plants. Since the compound has a ureido group (—NH-CONH—) in the molecule, it is considered that the compound is one kind of a urea series herbicidal composition represented by Diuron (3,4-dichloro-N,N-dimethylphenylurea) and the like. However, according to the conventional researches, since it has been known that a urea series herbicidal composition in which its ortho-position of a benzene ring is substituted by has remarkably less activity (see Nakamura Zassou Kenkyu, No. 3, p. 35), it is marvelous that, as in the compound of the present invention, the N-carbamoyl-3,4-dihydro-2H-1,4-benzoxazine derivative which is formed a ring between an ortho-position of a benzene ring and a nitrogen atom of a ureido group has excellent herbicidal effect due to its potent photosynthesis inhibiting ability.

We claim:

1. A 3,4-dihydro-2H-1,4-benzoxazine compound represented by the formula:

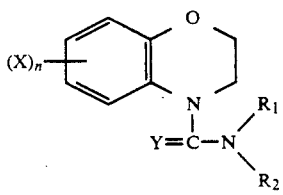

(I)

wherein X represents a hydrogen atom, an alkyl group having 1 to 5 carbon atoms, a halogen atom, a trifluoromethyl group, a phenoxy group or a halogen-substituted phenoxy group; n is 0, 1, 2 or 3; Y represents an oxygen atom or a sulfur atom; and R₁ and R₂ each represent a hydrogen atom or an alkyl group having 1 to 5 carbon atom, provided that the case where both of R₁ and R₂ are hydrogen atoms is excluded.

2. The 3,4-dihydro-2H-1,4-benzoxazine compound according to claim 1, wherein said compound is represented by the formula:

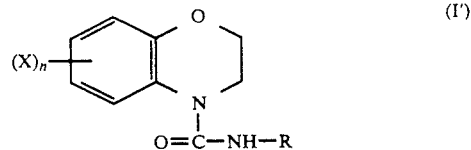

(I')

wherein X represents an alkyl group having 1 to 5 carbon atoms, a halogen atom or a trifluoromethyl group; n is 1 or 2; and R represents an alkyl group having 1 to 5 carbon atom.

3. The 3,4-dihydro-2H-1,4-benzoxazine compound according to claim 1, wherein said compound is one selected from the group consisting of 7-isopropyl-4-(N-methylcarbamoyl)-3,4-dihydro-2H-1,4-benzoxazine, 6-trifluoromethyl-4-(N-methylcarbamoyl)-3,4-dihydro-2H-1,4-benzoxazine, 6-chloro-7-methyl-4-(N-methylcarbamoyl)-3,4-dihydro-2H-1,4-benzoxazine, 6,7-dichloro-4-(N-methylcarbamoyl)-3,4-dihydro-2H-1,4-benzoxazine and 7-bromo-6-chloro-4-(N-methylcarbamoyl)-3,4-dihydro-2H-1,4-benzoxazine.

4. The compound of claim 1 designated 7-isopropyl-4-(N-methylcarbamoyl)-3,4-dihydro-2H-1,4-benzoxazine.

5. The compound of claim 1 designated 6-trifluoromethyl-4-(N-methylcarbamoyl)-3,4-dihydro-2H-1,4-benzoxazine.

6. The compound of claim 1 designated 6-chloro-7-methyl-4-(N-methyl-carbamoyl)-3,4-dihydro-2H-1,4-benzoxazine.

7. The compound of claim 1 designated 6,7-dichloro-4-(N-methylcarbamoyl)-3,4-dihydro-2H-1,4-benzoxazine.

8. The compound of claim 1 designated 7-bromo-6-chloro-4-(N-methylcarbamoyl)-3,4-dihydro-2H-1,4-benzoxazine.

9. A herbicidal composition which comprises an herbicidally effective amount of a 3,4-dihydro-2H-1,4-benzoxazine compound represented by the formula:

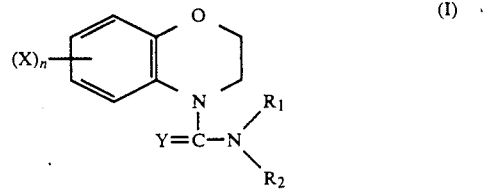

(I)

wherein X represents a hydrogen atom, an alkyl group having 1 to 5 carbon atoms, a halogen atom, a trifluoromethyl group, a phenoxy group or a halogen-substituted phenoxy group; n is 0,1,2 or 3; Y represents an oxygen atom or a sulfur atom; and R₁ and R₂ each represent a hydrogen atom or an alkyl group having 1 to 5 carbon atoms, provided that the case where both of R₁ and R₂ are hydrogen atoms is excluded, as an active ingredient together with a herbicidally acceptable carrier.

10. The herbicidal composition according to claim 9, wherein said compound is represented by the following formula:

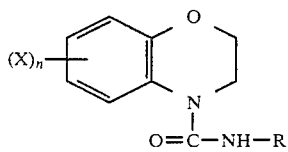

(I')

wherein X represents an alkyl group having 1 to 5 carbon atoms, a halogen atom or a trifluoromethyl group; n is 1 to 2; and R represents an alkyl group having 1 to 5 carbon atom.

11. The herbicidal composition according to claim 9, wherein said compound is one selected from the group consisting of 7-isopropyl-4-(N-methylcarbamoyl)-3,4-dihydro-2H-1,4-benzoxazine, 6-trifluoromethyl-4-(N-methylcarbamoyl)-3,4-dihydro-2H-1,4-benzoxazine, 6-chloro-7-methyl-4-(N-methylcarbamoyl)-3,4-dihydro-2H-1,4-benzoxazine, 6,7-dichloro-4-(N-methylcarbamoyl)-3,4-dihydro-2H-1,4-benzoxazine and 7-bromo-6-chloro-4-(N-methylcarbamoyl)-3,4-dihydro-2H-1,4-benzoxazine.

12. A method of combating weeds comprising applying an herbicidally effective amount of the compound of claim 1 to the foliage of weeds.

13. A method of combating weeds comprising applying an herbicidally effective amount of the compound of claim 2 to the foliage of weeds.

14. A method of combating weeds comprising applying an herbicidally effective amount of the compound of claim 3 to the foliage of weeds.

15. A method of combating weeds comprising applying an herbicidally effective amount of the compound of claim 4 to the foliage of weeds.

16. A method of combating weeds comprising applying an herbicidally effective amount of the compound of claim 5 to the foliage of weeds.

17. A method of combating weeds comprising applying an herbicidally effective amount of the compound of claim 6 to the foliage of weeds.

18. A method of combating weeds comprising applying an herbicidally effective amount of the compound of claim 7 to the foliage of weeds.

19. A method of combating weeds comprising applying an herbicidally effective amount of the compound of claim 8 to the foliage of weeds.

* * * * *